United States Patent [19]

Schoen et al.

[11] Patent Number: 4,771,044

[45] Date of Patent: Sep. 13, 1988

[54] TETRAOXO COMPOUNDS AND PHARMACEUTICAL COMPOSITIONS

[75] Inventors: Uwe Schoen, Burgdorf; Wolfgang Kehrbach, Hanover; Werner Benson, Seelze; Andreas Fuchs; Michael Ruhland, both of Hanover, all of Fed. Rep. of Germany

[73] Assignee: Kali-Chemie Pharma GmbH, Hanover, Fed. Rep. of Germany

[21] Appl. No.: 898,043

[22] Filed: Aug. 19, 1986

[30] Foreign Application Priority Data

Aug. 21, 1985 [DE] Fed. Rep. of Germany ....... 3529872

[51] Int. Cl.[4] ................. C07D 471/08; A61K 31/395; A61K 31/445
[52] U.S. Cl. .................................... 514/183; 540/453; 540/460; 540/463
[58] Field of Search ....................... 540/453, 460, 463; 514/183

[56] References Cited

U.S. PATENT DOCUMENTS 4,550,114  10/1985  Schoen et al. ...................... 514/183

FOREIGN PATENT DOCUMENTS 2658558  6/1978  Fed. Rep. of Germany ...... 514/183
3234697  3/1984  Fed. Rep. of Germany ...... 514/183

OTHER PUBLICATIONS

McElvain et al., "J. Am. Chem. Soc.", vol. 80, (1958), pp. 3915-3923.
Chemical Abstracts, vol. 54 (1960), Abstracting Handley et al., "Australian J. Chem., vol. 13, pp. 127-144 (1960).
Hoerlein et al., Chem. Ber. 110 (1977), pp. 3894 ff.
Hoerlein, Eur. J. Med. Chem., 1977, pp. 301-305.

Primary Examiner—Robert T. Bond
Attorney, Agent, or Firm—Foley & Lardner, Schwartz, Jeffery, Schwaab, Mack, Blumenthal & Evans

[57] ABSTRACT

Tetraoxo compounds of the Formula (I)

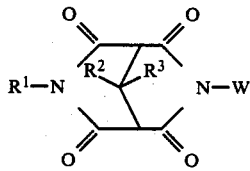

wherein
$R^1$ is an alkyl, alkenyl, phenylalkyl or cycloalkylalkyl group,
$R^2$ and $R^3$ are each independently an alkyl or phenyl group or together denote an alkylene group,
W is a $(CH_2)_n$—Q group, in which n is 2 to 10 and Q is
 (a) a displaceable leaving group X, or
 (b) Z-$R^4$, where Z is a 1-piperazinyl group, and $R^4$ is in position 4, and is hydrogen or a phenyl, substituted phenyl, N-heteroaryl or substituted N-heteroaryl group;

and salts and acid addition salts of said compound, and a method for their preparation. Selected compounds of Formula (I) have been found to have central nervous system affecting activity.

19 Claims, No Drawings

TETRAOXO COMPOUNDS AND PHARMACEUTICAL COMPOSITIONS

BACKGROUND OF THE INVENTION

This invention relates to new tetraoxo compounds, methods for their preparation, medicaments containing tetraoxo compounds and their pharmaceutically usable acid addition salts and to a method for the preparation of such medicaments.

The basic structure of the tetraoxo compounds according to the invention, namely that of 2,4,6,8-tetraoxo-3,7-diazabicyclo-(3,3,1)-nonane and its derivatives substituted in 3,7 and/or 9 position by alkyl or phenyl or in position 9 by alkylene, is already known. In this respect reference is made, for example, to Hoerlein, Eur. J. Med. Chem. 1977, pp. 301–5; Hoerlein et al., Chem. Ber. 110 (1977), pp. 3894 ff; McElvain et al., J. Amer. Chem. Soc. (1958) 80, pp. 3915 ff; DE-OS No. 26 58 558; and DE-OS No. 32 34 697, the disclosures of which are incorporated herein by reference.

SUMMARY OF THE INVENTION

It is an object of the invention to make available new tetraoxo compounds with advantageous pharmacological activities.

It is a further object of the invention to make available new tetraoxo compounds which are valuable intermediate products for the preparation of pharmacologically active tetraoxo compounds.

According to one aspect of the present invention there is provided a tetraoxo compound corresponding to Formula (I)

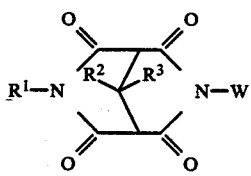

(I)

in which
- $R^1$ is an alkyl, alkenyl, phenylalkyl or cycloalkylalkyl group,
- $R^2$ and $R^3$ are each an alkyl or phenyl group or together denote an alkylene group;
- W is a $(CH_2)_n$—Q group, where n is 2 to 10 and Q is
  - (a) a displaceable leaving group X, or
  - (b) Z—$R^4$, where Z is a 1-piperazinyl group and $R^4$ is in position 4, and is hydrogen or a phenyl, substituted phenyl, N-heteroaryl or substituted N-heteroaryl group;

and salts and acid addition salts of said compounds.

In a preferred embodiment, the substitutent $R_1$ contains 1 to 12, preferably 1 to 7 carbon atoms.

Where $R^1$ is an alkyl group, it may be branched or unbranched alkyl. Examples of suitable unbranched alkyl groups include methyl, ethyl, n-propyl, n-butyl, n-pentyl, n-hexyl and n-heptyl groups, and examples of suitable branched alkyl groups include isopropyl, sec.-butyl (i.e. 2-methylpropyl), 3-methylbutyl, 2,2-dimethylpropyl, 2-methylpentyl and 3,3-dimethylbutyl groups. If $R^1$ is an alkenyl group, it may likewise be a branched or unbranched group, whereby the double bond is not adjacent to the N-atom group. Examples of suitable unbranched alkenyl groups include allyl (i.e. 2-propenyl), 2-butenyl, 3-butenyl, 2-pentenyl, 3-pentenyl and 4-pentenyl groups. Examples of suitable branched alkenyl groups include the 2-methyl-2-propenyl group.

In a further embodiment, $R^1$ may also contain a phenyl or a cycloalkyl substituent. In such case, the cycloalkyl group preferably contains 3 to 6 carbon atoms. The cycloalkyl or phenyl group is connected to the associated N-atom via an alkylene chain containing 1 to 6 carbon atoms, preferably 1 to 3 carbon atoms. Examples of such cycloalkyl groups include cyclopropyl, cyclobutyl, cyclopentyl and cyclohexyl groups. Preferably the cycloalkyl group is joined via a methylene group with the respective N-atom.

Where $R^2$ and $R^3$ are alkyl, particularly unbranched alkyl, the definitions given above for $R_1$ apply similarly. Preferably $R^2$ and $R^3$ in each case contain 1 to 7, more preferably 1 to 4, carbon atoms.

$R^2$ and $R^3$ may be the same or different, but it is preferred that $R^2$ and $R^3$ be the same.

In another preferred embodiment $R^2$ and $R^3$ together form an alkylene chain —$(CH_2)_m$—, in which m is preferably from 3 to 6, in particular 3 to 5.

A sub-group of compounds according to Formula (I) is characterized in that the group W represents $(CH_2)_n$—Q with Q=X. The compounds of this group are valuable intermediate products for the preparation of pharmacologically active tetraoxo compounds.

If, for simplification, the tetraoxo nucleus is represented in the following formula by "T", i.e. if the general form T-W is used for Formula (I), the above mentioned sub-group of compounds has the Formula (Ia)

where the coefficient n for the alkylene chain preferably has a value of 2 to 10, in particular 2 to 6, and where X is a displaceable leaving group, in particular a leaving group capable of being displaced by an amine.

Preferably, X is halogen, in particular chlorine or bromine, or a tosylate, mesylate, sulfate or phosphate group.

A further sub-group of compounds are those in which W represents $(CH_2)_n$—Z—H, i.e. compounds of the type represented by formula (Ib)

where T, n and Z have the meanings defined above.

These compounds are also valuable intermediate products for the preparation of pharmacologically active tetraoxo compounds.

Another sub-group of compounds are those in which W represents $(CH_2)_n$—Z—$R^6$, in which $R^6$ has the same meaning given above for $R^4$, except for hydrogen. These compounds therefore correspond to the Formula (Ic)

and these compounds possess valuable pharmacological properties.

In Formula (Ic) T, n, Z and $R^6$ have the previously given meanings in which $R^6$ is a phenyl, substituted phenyl, N-heteroaryl or substituted N-heteroaryl group, and in which N-heteroaryl is selected from 2-pyridyl, 4-pyridyl, 2-pyrimidyl or 2-pyrazinyl.

If $R^6$ is a substituted phenyl group, it is preferably monosubstituted. The following are particularly suitable substituents:

- alkyl, preferably 2-alkyl such as 2-methyl or 2-ethyl, or 3-alkyl such as 3-methyl or 3-ethyl, or 4-alkyl such as 4-methyl or 4-ethyl, or
- alkoxy, preferably 2-alkoxy such as 2-methoxy or 2-ethoxy, or hydroxy, preferably 2-hydroxy, or
- halogen, preferably 2-halogen such as 2-chloro or 2-fluoro, or 3-halogen such as 3-chloro, or 4-halogen such as 4-chloro or 4-fluoro, or
- nitro, preferably 2-nitro, or
- cyano, preferably 2-cyano, or
- trifluoromethyl, preferably 3-trifluoromethyl.

If $R^6$ is disubstituted, the following are particularly suitable substituents:

- 2,6-dialkyl, such as 2,6-dimethyl or 2,6-diethyl, or
- 3,4-dihydroxy, 3,4-dialkoxy, 3,4-methylene dioxy, 3,4-ethylene dioxy, 3-trifluoro-4-halogen, in particular 3-trifluoro-4-chloro.

If $R^6$ is an N-heteroaryl group, it is preferably monosubstituted, and, for example, where $R^6$ is 2-pyridyl, suitable substituents include:

- alkyl, preferably 5-alkyl such as 5-methyl or 5-ethyl, or 4-alkyl such as 4-methyl or 4-ethyl, or
- nitro, preferably 5-nitro, or
- halogen, preferably 5-halogen, such as 5-chloro, or
- alkoxy, preferably 6-alkoxy, such as 6-methoxy or 6-ethoxy.

Particularly preferred compounds from this group corresponding to the general Formula (Ic) are those with the following combinations of substituents:

| $R^1$ | $R^2$ and $R^3$ | $R^4$ |
|---|---|---|
| Alkyl, optionally substituted by cycloalkyl | (a) Alkyl (b) Alkylene (c) Aryl | Phenyl, optionally substituted |
| (Phenyl)-alkyl | (a) Alkyl (b) Alkylene (c) Aryl | Phenyl, optionally substituted |
| Alkenyl | (a) Alkyl (b) Alkylene (c) Aryl | Phenyl, optionally substituted |
| Alkyl, optionally substituted by cycloalkyl | (a) Alkyl (b) Alkylene (c) Aryl | Optionally substituted 2-pyridyl or 4-pyridyl |
| (Phenyl)-alkyl | (a) Alkyl (b) Alkylene (c) Aryl | Optionally substituted 2-pyridyl or 4-pyridyl |
| Alkenyl | (a) Alkyl (b) Alkylene (c) Aryl | Optionally substituted 2-pyridyl or 4-pyridyl |
| Alkyl, optionally substituted by cycloalkyl | (a) Alkyl (b) Alkylene (c) Aryl | Optionally substituted 2-pyrimidyl or 2-pyrazinyl |
| (Phenyl)-alkyl | (a) Alkyl (b) Alkylene (c) Aryl | Optionally substituted 2-pyrimidyl or 2-pyrazinyl |
| Alkenyl | (a) Alkyl (b) Alkylene (c) Aryl | Optionally substituted 2-pyrimidyl or 2-pyrazinyl |

The same preferred substituent combinations for $R^1$ and also $R^2$ and $R^3$ apply similarly to compounds of the general Formulae (Ia) and (Ib).

Salts and acid addition salts of the compounds of Formula (I) are also within the scope of the invention.

As used herein, "salts" denotes true salts, e.g. of compounds of type (Ib) with, in particular, sodium or lithium, or salts which are formed with substituents located on the aromatic ring, which are capable of salt formation, such as, for example, phenolate salts.

Acid addition salts are obtained by reaction of the basic compounds of Formula (I) in a known manner with acids. Particularly preferred are the acid addition salts of compounds of Formula (Ic) with pharmaceutically acceptable acids.

Suitable pharmaceutically usable acid addition salts include, for example, water-soluble and water-insoluble salts of inorganic or organic acids, such as, for example, the hydrochloride, hydrobromide, hydroiodide, phosphate, nitrate, sulfate, perchlorate, acetate, citrate, gluconate, benzoate, propionate, butyrate, sulfosalicylate, maleinate, laurate, fumarate, succinate, oxalate, tartrate, stearate, tosylate (p-toluene sulfonate), 2-hydroxy-3-naphthoate, 3-hydroxy-2-naphthoate, mesylate (methane sulfonate) and naphthalene sulfonate.

The invention also relates to medicaments containing at least one compound of Formula (Ic) or a pharmaceutically usable acid addition salt thereof, and to a method for preparing such medicaments, in which at least one of the aforementioned pharmaceutically active tetraoxo compounds is mixed with at least one inert, pharmaceutically acceptable carrier substance and the mixture is converted in a known manner into a galenical preparation. Such preparations may include, for example, tablets, dragees, capsules, powders, granulates, aqueous and oily suspensions, emulsions, syrups or solutions for oral administration, suppositories for rectal administration or sterile injectable suspensions or solutions for parenteral application.

According to another aspect of the present invention there is provided a method for preparing a compound of Formula (I) as defined above, in which a compound of the formula

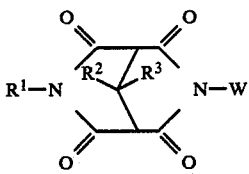

in which $R^1$, $R^2$ and $R^3$ have the meanings defined above and W is a hydrogen atom, a $-(CH_2)_n-Z-X$ group where X is a displaceable leaving group, or a $-(CH_2)_n-Z-H$ group where Z is a 1-piperazinyl group and n is 2 to 10, is reacted with a compound of the general Formula (II)

$$Y-R^5 \quad \quad (II)$$

in which Y and $R^5$ have the following meanings:
(a) if W is a hydrogen atom, then
 (a1) Y is a displaceable leaving group X, and $R^5$ is a $-(CH_2)_n-Q$ group where Q is a displaceable leaving group X, or $Z-R^4$ where $R^4$ is in position 4 and is hydrogen or a phenyl, substituted phenyl, N-heteroaryl or substituted N-heteroaryl group, or
 (a2) if n=4, then Y may be a

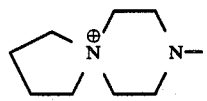

group, and $R^5$ is an $R^6$ group selected from phenyl, substituted phenyl, N-heteroaryl or substituted N-heteroaryl groups, (b) if W is a —$(CH_2)_n$—X group, then Y is a hydrogen atom and $R^5$ is a —Z—$R^4$ group where Z and $R^4$ have the meanings defined above, or (c) if W is a —$(CH_2)_n$—Z—H group, Y is a nucleophilically displaceable leaving group V, preferably fluorine, chlorine or bromine and $R^5$ is an activated phenyl group, an N-heteroaryl group or a substituted N-heteroaryl group.

The foregoing general process embodiments (a), (b) and (c) represent a unified method for preparing compounds of Formula (I), in which W represents $(CH_2)_n$—Q, as described above, wherein a compound of the general formula T-H (Id), (Ia) or (Ib) is reacted with an appropriate intermediate of Formula (II) in a solvent which is inert under the reaction conditions.

Some of the compounds of Formula T-H (Id) which are used as starting materials are known from the aforementioned technical literature. To the extent they are new, they may be prepared in a manner analagous to the methods used to prepare the known compounds. Likewise, the compounds of Formula (II) are either already known, or they may be easily synthesized by routine adaptations of known processes.

Process embodiments (b) and (c) are conventionally carried out under reaction conditions which are used to prepare tertiary amines by alkylation of secondary amines. Thus the compounds of Formula (I) are obtained by reacting suitable intermediate products T-H (Id), (Ia) or (Ib) with a compound of Formula (II) in an inert reaction medium at temperatures of approximately 20° C. to approximately 200° C. in the presence of a base which is capable of being used as an acid-binding agent. Inorganic and organic acid-binding bases which can be used include tertiary amines, preferably triethyl amine; alkali and alkaline earth metal carbonates, bicarbonates or hydrides, sodium carbonate and potassium carbonate being particularly preferred. The term "inert reaction medium" refers to every protic or aprotic solvent or diluent which does not enter into the reaction to any substantial degree. In this respect, dimethylformamide is a particularly preferred solvent, whereby the reaction is carried out in a suitable manner at reflux temperature.

In process embodiment (c), as described above, a compound of Formula (Ib) is reacted with a compound of Formula (II). In this embodiment, substituted aromatic compounds are to be understood as compounds of Formula (II) in which Y is a displaceable, in particular a nucleophilically displaceable, leaving group V. Preferred leaving groups V are halogens, such as fluorine, chlorine, bromine. The substituent $R^5$ in this embodiment is an activated phenyl, N-heteroaryl or substituted N-heteroaryl group. "Activated phenyl" means phenyl which is substituted in the ortho and/or para position with electron-withdrawing groups.

Satsfactory yields of compounds according to the invention are obtained with reaction times of approximately 2 to 24 hours. Products of Formula (I) may be obtained by crystallization from standard solutions in solvents such as acetonitrile, isopropanol, methanol, ethanol and the like, or by any other conventional method such as chromatography using a silica gel or an alumina column with a mixture of acetate ester, hexane or alkanols, such as methanol and ethanol, as the elution agent.

In process embodiment (a), a salt, preferably an alkali metal salt of the imide of Formula (Id) is alkylated. Conventional laboratory methods are used to carry out this reaction, such as are used, for example, for alkylation in the Gabriel synthesis. In the present case, for example, the reactants are reacted in an inert reaction medium at a temperature from 50° C. to 200° C. Toluene, xylene and/or dimethylformamide are particularly preferred solvents for carrying out the reaction, but any other solvents which do not adversely affect the reaction or the reactants, may also be used. Solvents such as dioxane, benzene, acetone, acetonitrile, n-butanol and the like are suitable. In general, the alkali metal salts of compounds of Formula (Id) are prepared by reacting the corresponding imide precursor with an alkali hydride, such as sodium hydride, an alkali alcoholate, such as sodium ethoxide, an alkali amide, such as sodium amide, an alkali base, such as sodium hydroxide or potassium hydroxide, or an alkali carbonate, such as sodium carbonate or potassium carbonate, in a suitable solvent. It is not necessary to prepare the alkali metal salts of Formula (IV) separately in advance; they may also be produced in situ.

In a further variation of embodiment (a), suitable intermediate products of Formula T-H (Id), (Ia) or (Ib) are reacted with a compound of Formula (II) in an inert reaction medium at a temperature from approximately 20° C. to approximately 220° C. in the presence of a base, which can be used as an acid-binding agent. Organic, acid-binding bases which can be used include tertiary amines, preferably triethylamine.

In variant embodiment (a1), the corresponding compound of Formula (II) is used as the alkylation agent. In a variant embodiment (a2) of this method, for cases where n=4, the 8-aza-5-azoniaspiro-(4,5)-decane-salt, substituted accordingly in position 8, is used as the alkylation agent, i.e. a compound with a cation having the structure

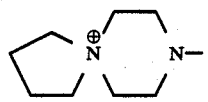

in which the anion may be a conventional salt residue, in particular bromide.

The compounds of Formula (Ic) according to the invention possess valuable pharmacological properties. Thus they affect the central nervous system.

Mammals (humans and animals) may be treated with the compounds of Formula (Ic) according to the invention. For this, the mammal which is to be treated is administered systemically with a therapeutically effective quantity of a compound of the general Formula (Ic) or of a pharmaceutically acceptable acid addition salt thereof. An effective dose is from approximately 0.01 to 40 mg/kg body weight, the dosaging depending upon which effects one wishes to achieve, which manner of administration is selected and which compound is used. A preferred dosage range is approximately 0.5 to 1.5 mg/kg per day, administered in divided doses. "Systemic administration" is understood to mean an oral, rectal or parenteral (i.e. intramuscular, intravenous and subcutaneous) administration. If a compound according to the invention is administered orally, then it is generally necessary to use a larger quantity of the active substance in order to achieve the same effect which can be achieved with a smaller parenterally administered amount. The compounds according to the invention are preferably administered in concentrations such that efficacious effects are brought about, without thereby causing harmful or undesired side effects.

The invention will now be illustrated by the following examples which are intended to explain the preparation of the new compounds in further detail, but not to restrict the scope of the invention in any way.

EXAMPLE 1

Process Embodiment (a1): Conversion of compounds of Formula (Id) to compounds of Formula (Ia)

Embodiment (A)

A solution of 0.1 mole tetraoxo compound of Formula (Id), 0.1 mole 1,ω-dibromoalkane and 0.12 mole triethylamine in 200 ml dimethylformamide was allowed to react at ambient temperature overnight. The sediment produced during the reaction was separated by filtration. After distilling off the solvent, the remaining residue was taken up in methylene chloride and washed with water several times. The organic phase was dried over MgSO4; the drying agent was filtered out, and the volume of the solution was reduced. The resulting oil may be further reacted without additional purification.

Embodiment (B)

A mixture of 0.1 mole tetraoxo compound of Formula (Id), 0.15 mole 1,ω-dibromoalkane and 0.25 mole potassium carbonate in 200 ml dimethylformamide was heated overnight under reflux. After drawing off the solvent, the remaining residue was taken up with water and methylene chloride. After separation from the organic phase, the aqueous phase was washed again twice with methylene chloride. The combined organic extracts were dried over MgSO4. The drying agent was filtered out, and the oily product of Formula (Ia) as described above was obtained.

As examples, the compounds designated in Table 1 by process embodiment (a1A) or (a1B) were produced according to these procedures.

EXAMPLE 2

Process Embodiment (a2): Conversion of compounds of Formula (Id) to compounds of Formula (Ic)

0.1 mole tetraoxo compound of Formula (Id), 0.1 mole 8-(aryl or heteroaryl)-8-aza-5-azoniaspiro-(4,5)-decane bromide and 0.12 mole sodium carbonate were heated in 500 ml dimethylformamide for 24 hours under reflux. After drawing off the solvent, the remaining residue was taken up with water and alkalized with 10% aqueous sodium hydroxide. The aqueous phase was extracted several times with methylene chloride. After drying the combined organic extracts over magnesium sulfate and filtering out the drying agent, the easily volatile constituents were distilled off.

If necessary, further purification may be carried out by column chromatography on silica gel or aluminum oxide with acetate ester/hexane mixtures. If, however, the desired compound is obtained in crystalline form, a simple recrystallization process is sufficient for further purification.

The compounds of Formula (Id) can be reacted with a pharmaceutically acceptable acid to form a salt of the compound.

Following this procedure, for example, the compounds designated in Table 3 by process embodiment (a2) were produced.

EXAMPLE 3

Process Embodiment (b): Conversion of compounds of Formula (Ia) to compounds of Formula (Ib)

A mixture of 0.1 mole of compound of Formula (Ia), 1 mole anhydrous piperazine and 0.125 mole triethylamine was reacted overnight at ambient temperature in 200 ml dimethylformamide. The volume of the reaction solution was reduced under vacuum, and the residue was distributed between water and methylene chloride. The organic phase was separated. After filtering out the drying agent, the organic solution was concentrated in vacuum to an oil, which was subsequently dissolved in ethanol and reacted with ethanolic hydrochloric acid. Compounds prepared according to this procedure are indicated by process embodiment (b) in Table 2.

EXAMPLE 4

Process Embodiment (b): Conversion of compounds of Formula (Ia) to compounds of Formula (Ic)

Embodiment (A)

A mixture of 0.1 mole of compound of Formula (Ia), 0.1 mole of compound of Formula (II) and 0.125 mole triethylamine was reacted overnight in 200 ml dimethylformamide. If a sediment was produced during the reaction, it was removed by filtration. The clear solution was concentrated to dryness. The remaining residue was distributed between water and methylene chloride. The organic phase was separated, washed twice with water and drid over MgSO4. After filtering out the drying agent, the organic solution was concentrated.

If necesssary, further purification may be carried out by column chromatography on silica gel or aluminum oxide with acetate ester/hexane mixtures. If, however, the desired compound is obtained in crystalline form, a simple recrystallization process is sufficient for further purification.

Embodiment (B)

A mixture of 0.1 mole of compound of Formula (Ia), 0.1 mole of compound of Formula (II) and 0.25 mole potassium carbonate in 250 ml dimethylformamide was heated overnight under reflux. After drawing off the solvent, the residue was distributed between water and methylene chloride. Further working up was carried out as described above under embodiment (A).

The compounds denoted in Table 3 by process embodiment (bA) or (bB), for example, were prepared according to these two procedures, respectively.

EXAMPLE 5

Process Embodiment (a1): Conversion of compounds of Formula (Id) to compounds of Formula (Ic)

A mixture of 0.1 mole of compound of Formula (Id), 0.1 mole of compound of Formula (II) and 0.12 mole sodium carbonate was heated in 300 ml dimethylformamide for 7 hours at reflux. After removal of the solvent, the remaining residue was taken up in water and alkalized with 10% aqueous sodium hydroxide. The aqueous phase was extracted several times with methylene chloride. After drying the combined organic extracts over MgSO4, the easily volatile constituents were distilled off. The remaining oil was dissolved in isopropanol and mixed with hydrochloric acid dissolved in isopropanol.

As examples, the compounds denoted in Table 3 by process embodiment (a1C) were prepared according to this procedure.

EXAMPLE 6

Process Embodiment (c): Conversion of compounds of Formula (Ib) to compounds of Formula (Ic)

A mixture of 0.05 mole of compound No. 2101 (base as an example of a compound of Formula (Ib), 0.05 mole 2-chloropyrimidine as an example of a compound of Formula (II) and 0.1 mole potassium carbonate was heated overnight in 200 ml acetonitrile at reflux. After removing the solvent, the remaining residue was distributed between water and methylene chloride. The organic phase was separated and dried over $MgSO_4$. After filtering out the drying agent, the organic solution was concentrated under vacuum. The remaining oil was dissolved in ethanol and mixed with ethanolic hydrochloric acid. The isolated salt (compound 3304) contains 2.1 equivalents of HCl and melts between 216° and 218° C.

The compounds designated in Table 3 by process embodiment(s) were prepared in a manner analogous to this procedure.

EXAMPLE 7—TABLETS

| Composition: | |
|---|---|
| Active substance No. 3209 | 20 parts |
| Cornstarch | 30 parts |
| Lactose | 55 parts |
| Polyvinylpyrrolidone "Kollidon" 25 | 5 parts |
| Magnesium stearate | 2 parts |
| Hydrated castor oil | 1 part |
| Total | 113 parts |

Directions for preparation:

The active substance was mixed with the cornstarch and finely powdered lactose in a mixer. The resulting mixture was thoroughly moistened with a 20% solution of polyvinylpyrrolidone ("Kollidon" ®25, from BASF) in isopropanol. If necessary, further isopropanol may be added. The moist granulate was passed through a 2 mm sieve, dried at 40° C. on hurdle racks and then passed through a 1 mm sieve (Frewitt machine). After mixing the granulate with magnesium stearate and hydrated castor oil, tablets of 113 mg were compressed therefrom, so that each tablet contained 20 mg of active substance.

EXAMPLE 8—CAPSULES

| Composition: | |
|---|---|
| Active substance No. 3209 | 20 parts |
| Cornstarch | 20 parts |
| Lactose | 45 parts |
| Polyvinylpyrrolidone "Kollidon" 25 | 3 parts |
| Magnesium stearate | 1.5 parts |
| Silica aerogel "Aerosil" 200 | 0.5 part |
| Total | 90 parts |

Directions for preparation:

The active substance was mixed with the cornstarch and finely powdered lactose in a mixer. The resulting mixture was thoroughly moistened with a 20% solution of polyvinylpyrrolidone ("Kollidon" ®25, from BASF) in isopropanol. If necessary, further isopropanol may be added. The moist granulate was passed through a 1.6 mm sieve (Frewitt), dried at 40° C. on hurdle racks and then passed through a 1 mm sieve (Frewitt). After mixing the granulate with magnesium stearate and silica aerogel ("Aerosil" ®200, from Degussa), 90 mg portions were filled by means of an automatic capsule machine into size 4 hard gelatine capsules, so that each capsule contained 20 mg of active substance.

EXAMPLE 9—Ampoules

| Composition per ampoule: | |
|---|---|
| Active substance No. 3209 | 5 mg |
| Sodium chloride | 16 mg |
| Water for injection purposes | ad 2.0 ml |

Directions for preparation:

Sodium chloride was dissolved in water for injection purposes, and the active compound was added and dissolved with stirring. Filling takes place up to the final volume with sufficient water for injection purposes. The formulation was passed through a 0.25 micron membrane filter. In each case 2.15 ml were filled into brown glass ampoules, and the ampoules were sealed by melting. Sterilization was carried out by steam at 121° C. for 30 minutes. 2 ml of injection solution contain 5 mg of active substance.

In addition to the terms already mentioned, the following abbreviations are used in the following tables:
B=base, S=salt, Ph=phenyl, Py=pyridyl, Pm=pyrimidyl, Pz=pyrazinyl, ch=cyclohexyl.

Thus, for example, a 2-methoxyphenyl substituent is designated as Ph-2-OCH$_3$ and 4-methyl-2-pyridyl is designated as 2-Py-4-CH$_3$.

TABLE 1

Compounds of Type (Ia)

| No. | $R^1$ | $R^2$ | $R^3$ | n | Q | Melting Point (°C.) | Process Embodiment |
|---|---|---|---|---|---|---|---|
| 1101 | $C_2H_5$ | $CH_3$ | $CH_3$ | 4 | Br | 125-127 | aIA |
| 1102 | n-$C_4H_9$ | $CH_3$ | $CH_3$ | 2 | Br | 71-74 | aIB |
| 1103 | n-$C_4H_9$ | $CH_3$ | $CH_3$ | 3 | Br | 77-79 | aIA |
| 1104 | n-$C_4H_9$ | $CH_3$ | $CH_3$ | 4 | Br | oil | aIA |
| 1105 | n-$C_4H_9$ | $CH_3$ | $CH_3$ | 5 | Br | 65-69 | aIA |
| 1106 | n-$C_4H_9$ | $CH_3$ | $CH_3$ | 4 | Br | 45-48 | aIA |
| 1107 | n-$C_4H_9$ | $CH_3$ | $CH_3$ | 5 | Br | 52-55 | aIA |

TABLE 2

Compounds of Type (Ib)

| No. | $R^1$ | $R^2$ | $R^3$ | n | Melting Point (°C.) Base/Salt | Process Embodiment |
|---|---|---|---|---|---|---|
| 2101 | n-$C_4H_9$ | $CH_3$ | $CH_3$ | 4 | S (2 HCL) 202-205 | b |

TABLE 3

Compounds of Type (Ic)

| No. | $R^1$ | $R^2$ | $R^3$ | $R^4$ | n | Melting Point (°C.) Base/Salt | Process Embodiment |
|---|---|---|---|---|---|---|---|
| 3101 | $C_2H_5$ | $CH_3$ | $CH_3$ | Ph—2-OCH$_3$ | 4 | B: 125-129 | bA |
| 3102 | n-$C_4H_9$ | $CH_3$ | $CH_3$ | Ph | 3 | B: 106 | bA |
| 3103 | n-$C_4H_9$ | $CH_3$ | $CH_3$ | Ph | 4 | B: 110-112 | bB |
| 3104 | n-$C_4H_9$ | $CH_3$ | $CH_3$ | Ph | 5 | B: 80-82 | bA |
| 3105 | n-$C_4H_9$ | $CH_3$ | $CH_3$ | Ph—2-OCH$_3$ | 2 | B: 125-128 | bB |

TABLE 3-continued
Compounds of Type (Ic)

| No. | R¹ | R² | R³ | R⁴ | n | Melting Point (°C.) Base/Salt | Process Embodiment |
|---|---|---|---|---|---|---|---|
| 3106 | n-C₄H₉ | CH₃ | CH₃ | Ph—2-OCH₃ | 3 | B: 100 | bA |
| 3107 | n-C₄H₉ | CH₃ | CH₃ | Ph—2-OCH₃ | 4 | B: 103–105 | bB |
| 3108 | n-C₄H₉ | CH₃ | CH₃ | Ph—2-OCH₃ | 5 | B: 80–82 | bB |
| 3109 | n-C₄H₉ | CH₃ | CH₃ | Ph—2-OCH₃ | 6 | B: 62–67 | bA |
| 3110 | n-C₄H₉ | CH₃ | CH₃ | Ph—2-OC₂H₅ | 4 | B: 100–102 | bA |
| 3111 | n-C₄H₉ | CH₃ | CH₃ | Ph—2-OC₂H₅ | 5 | B: 236–240 | bA |
| 3112 | n-C₄H₉ | CH₃ | CH₃ | Ph—2-CH₃ | 3 | B: 220–230 | bB |
| 3113 | n-C₄H₉ | CH₃ | CH₃ | Ph—2-CH₃ | 4 | B: 103–105 | a2 |
| 3150 | sec C₄H₉ | CH₃ | CH₃ | Ph—2-OCH₃ | 4 | B: 130–132 | a2 |
| 3151 | CH₂—ch | CH₃ | CH₃ | Ph—2-OCH₃ | 4 | S: (1 WS) 86–90 | a2 |
| 3176 | CH₂—Ph | CH₃ | CH₃ | Ph—2-OCH₃ | 4 | B: 129–131 | a2 |
| 3181 | CH₂—Ph | —(CH₂)₅— | | Ph—2-OCH₄ | 4 | S: (1 WS) 103–106 | a2 |
| 3114 | n-C₄H₉ | CH₃ | CH₃ | Ph—2-Cl | 3 | B: 86–90 | bA |
| 3115 | n-C₄H₉ | CH₃ | CH₃ | Ph—2-Cl | 4 | B: 122–124 | a2 |
| 3116 | n-C₄H₉ | CH₃ | CH₃ | Ph—2-NO₂ | 4 | oil | bA |
| 3117 | n-C₄H₉ | CH₃ | CH₃ | Ph—2-NO₂ | 5 | B: 90–92 | bA |
| 3118 | n-C₄H₉ | CH₃ | CH₃ | Ph—2-CN | 4 | B: 158–160 | bA |
| 3119 | n-C₄H₉ | CH₃ | CH₃ | Ph—2-CN | 5 | B: 233–235 | bA |
| 3120 | n-C₄H₉ | CH₃ | CH₃ | Ph—2-OH | 4 | S (HBr) 236–238 | bA |
| 3121 | n-C₄H₉ | CH₃ | CH₃ | Ph—2-OH | 5 | S (HBr) 175–180 | bA |
| 3122 | n-C₄H₉ | CH₃ | CH₃ | Ph—2,6-(CH₃)₂ | 4 | B: 123–127 | bA |
| 3123 | n-C₄H₉ | CH₃ | CH₃ | Ph—3-CH₃ | 3 | B: 202–205 | bA |
| 3124 | n-C₄H₉ | CH₃ | CH₃ | Ph—3-CH₃ | 4 | B: 115 | a2 |
| 3126 | n-C₄H₉ | CH₃ | CH₃ | Ph—3-CH₃ | 5 | oil | bA |
| 3127 | n-C₄H₉ | CH₃ | CH₃ | Ph—3-OCH₃ | 4 | oil | a2 |
| 3128 | n-C₄H₉ | CH₃ | CH₃ | Ph—3-Cl | 3 | B: 89–92 | bB |
| 3129 | n-C₄H₉ | CH₃ | CH₃ | Ph—3-Cl | 4 | B: 120 | a2 |
| 3130 | n-C₄H₉ | CH₃ | CH₃ | Ph—3-CF₃ | 4 | oil | bA |
| 3131 | n-C₄H₉ | CH₃ | CH₃ | Ph—4-CH₃ | 3 | B: 116–118 | bA |
| 3132 | n-C₄H₉ | CH₃ | CH₃ | Ph—4-CH₃ | 4 | B: 125–128 | a2 |
| 3133 | n-C₄H₉ | CH₃ | CH₃ | Ph—4-Cl | 3 | B: 255–260 | bB |
| 3134 | n-C₄H₉ | CH₃ | CH₃ | Ph—4-Cl | 4 | B: 134 | a2 |
| 3135 | n-C₄H₉ | CH₃ | CH₃ | Ph—4-F | 4 | oil | bB |
| 3136 | n-C₄H₉ | CH₃ | CH₃ | Ph—4-OCH₃ | 4 | B: 128–130 | bB |
| 3137 | n-C₄H₉ | CH₃ | CH₃ | Ph—3-CF₃—4-Cl | 4 | oil | bB |
| 3138 | n-C₄H₉ | CH₃ | CH₃ | Ph—3,4-(OCH₂O) | 4 | B: 125–127 | bB |
| 3139 | n-C₆H₁₃ | CH₃ | CH₃ | Ph | 4 | B: 57 | bA |
| 3140 | n-C₆H₁₃ | CH₃ | CH₃ | Ph | 5 | B: 68–70 | bA |
| 3141 | n-C₆H₁₃ | CH₃ | CH₃ | Ph—2-OCH₃ | 4 | B: 103–105 | bA |
| 3142 | n-C₆H₁₃ | CH₃ | CH₃ | Ph—2-OCH₃ | 5 | B: 74–76 | bA |
| 3146 | n-C₆H₁₃ | CH₃ | CH₃ | Ph—3-CH₃ | 4 | B: 103–105 | bA |
| 3143 | n-C₆H₁₃ | CH₃ | CH₃ | Ph—3-CH₃ | 5 | B: 86–89 | bA |
| 3144 | n-C₆H₁₃ | CH₃ | CH₃ | Ph—4-F | 4 | B: 66–68 | bA |
| 3145 | n-C₆H₁₃ | CH₃ | CH₃ | Ph—4-F | 5 | B: oil | bA |
| 3201 | C₂H₅ | CH₃ | CH₃ | 2-Py | 4 | B: 124–125 | bA |
| 3202 | n-C₄H₉ | CH₃ | CH₃ | 2-Py | 2 | B: 111–114 | bB |
| 3203 | n-C₄H₉ | CH₃ | CH₃ | 2-Py | 3 | S (3 WS) 78–84 | bB |
| 3204 | n-C₄H₉ | CH₃ | CH₃ | 2-Py | 4 | S (3 WS) 87–90 | a2 |
| 3205 | n-C₄H₉ | CH₃ | CH₃ | 2-Py | 5 | S (3,1 WS) 74–77 | bB |
| 3206 | n-C₄H₉ | CH₃ | CH₃ | 2-Py | 6 | B: 106–109 | bA |
| 3207 | n-C₄H₉ | CH₃ | CH₃ | 4-Py | 4 | S (2,9 WS) 93–97 | bA |
| 3208 | n-C₄H₉ | CH₃ | CH₃ | 2-Py-4-CH₃ | 3 | S (3 WS) 89–95 | bB |
| 3209 | n-C₄H₉ | CH₃ | CH₃ | 2-Py-4-CH₃ | 4 | S (3 WS) 105–110 | bB |
| 3210 | n-C₄H₉ | CH₃ | CH₃ | 2-Py-5-CH₃ | 4 | B: 110–112 | bA |
| 3211 | n-C₄H₉ | CH₃ | CH₃ | 2-Py-5-Cl | 4 | B: 113–115 | bA |
| 3212 | n-C₄H₉ | CH₃ | CH₃ | 2-Py-5-NO₂ | 4 | B: 97–99 | bA |
| 3213 | n-C₄H₉ | CH₃ | CH₃ | 2-Py-6-OCH₃ | 4 | B: 113–116 | bA |
| 3261 | n-C₄H₉ | —(CH₂)₄— | | 2-Py | 4 | S (3 WS) 128–132 | bB |
| 3262 | n-C₄H₉ | —(CH₂)₅— | | 2-Py | 4 | S (WS) 155–165 | a2 |
| 3301 | C₂H₅ | CH₃ | CH₃ | 2-Pm | 4 | B: 142–144 | bA |
| 3302 | n-C₄H₉ | CH₃ | CH₃ | 2-Pm | 2 | S: (1,8HCl) 210–212 | aIC, bA |
| 3303 | n-C₄H₉ | CH₃ | CH₃ | 2-Pm | 3 | B: 107–108 | bA |
| 3304 | n-C₄H₉ | CH₃ | CH₃ | 2-Pm | 4 | S (2,1HCl) 216–218 | c: bB |
| 3305 | n-C₄H₉ | CH₃ | CH₃ | 2-Pm | 5 | S (1,4HCl) 184–186 | bA |
| 3306 | n-C₄H₉ | CH₃ | CH₃ | 2-Pm | 6 | S (1,7HCl) 129 | bA |
| 3307 | n-C₄H₉ | CH₃ | CH₃ | 2-Pz | 4 | B: 103–105 | bA |
| 3361 | n-C₄H₉ | —(CH₂)₄— | | 2-Pm | 4 | S(2,5 HCl) 205–207 | bB |
| 3362 | n-C₄H₉ | —(CH₂)₅— | | 2-Pm | 4 | S(2HCl) 215–217 | bB |

As already mentioned above the compounds of formula Ic and their pharmacologically acceptable acid addition salts possess valuable pharmacological properties. In particular they possess central nervous system activities and advantageous social behavior influencing properties and exhibit a favorable psychopharmacological activity profile including antipsychotic, antidepressive and anxiolytic activity components and low toxicity.

The psychopharmacological properties of the compounds are demonstrated in following pharmacological standard tests in animals.

Description of Pharmacological Test Methods. In the following tables giving the test results the numbers given for the compounds of formula Ic refer to the preceding synthesis examples.

1. Determination of Minimum Toxic Dose

Male mice weighing 20 to 25 g are administered per os and i.p. maximum doses of 300 mg/kg of the test substances. The animals are carefully observed for three hours for toxic symptoms. During a period of 24 hours following the administration all symptoms and deaths are recorded. Side reactions are likewise observed and recorded. When death or strong toxic symptoms are observed, further mice are administered increasingly smaller doses. The lowest dose which produces death or strong toxic symptoms is given as the minimum toxic dose.

| Compound No. | Minimum Toxic Dose mg/kg mouse | |
|---|---|---|
| | p.o. | i.p. |
| 3135 | >300 | >300 |
| 3143 | >300 | >300 |
| 3107 | >300 | 200 |
| 3110 | >300 | >300 |

2. Evaluation of antipsychotic properties in the CAR-test procedure in rats.

In order to demonstrate the antipsychotic properties of the compounds, their inhibiting effects on a conditioned avoidance response in rats is shown.

The CAR test is performed in a modification of the experimental set up described by Capaldi et al (see R. D. Myers (ed): Methods in Psychobiology, Academic Press, New York, pp. 71-74). Fully automated one-way shuttle boxes are used, which are divided into 2 compartments by a wall with a hole. The floor of the box is a grid of stainless steel through which electric stimuli can be delivered. The ceiling of the box is provided with a lamp and a loudspeaker giving a buzzertone. In order to avoid the electric stimulus in the first starting compartment the animals can cross over into the safe second compartment.

During the test procedure the animals are placed into the starting compartment and at the same time the light and the loudspeaker are switched on as a warning signal (=conditioned stimulus). If at this warning signal already the animals cross over into the safe compartment, this is considered a CAR and is automatically recorded. If the animals don't cross over into the safe compartment within 5 sec. an electric shock is delivered additionally through the floor grid (=unconditioned stimulus) for a period of up to 15 sec. If at the presentation of the electric shock the animals cross over into the safe compartment, this is considered an unconditioned escape response (=UER). As soon as the animals have crossed over into the safe compartment the stimuli are switched off automatically.

For the test female Wistar rats having a body weight of 140–210 g are used. They are trained in a 20 trial session on the day before and only such animals which show CAR exclusively are used for the drug experiments.

Groups of 4 animals are used for each dose of the test compounds, the animals are placed into the test situation 15 times each, and the average value of the last 10 trials is taken into account.

The test compounds are administered per os in a volume of 10 ml/kg of 2% tylose solution one hour prior to testing. To a control group tylose solution only is administered. The dose which reduces CAR by 50% and thus leads to a 50% avoidance block is determined (=ED$_{50}$AB). Furthermore the dosis which reduces UER by 50% and thus leads to a 50% escape block is determined (=ED$_{50}$EB). The results are given in the table below.

| Compound No. | Antipsychotic activity | |
|---|---|---|
| | ED$_{50}$ AB μmol/kg | ED$_{50}$ EB μmol/kg |
| 3107 | 27 | 70 |
| 3110 | 50 | 200 |
| 3150 | 57 | >215 (215 = 43% EB) |

The compounds show a favorable AB/EB ratio.

3. Evaluation of antidepressive properties.

For demonstrating the antidepressive properties of the compounds it is shown that they possess an increasing effect on the central actions of subthreshold doses of 5-hydroxytryptophane (=5-HTP). This effect is typical of antidepressives. For this a modified method according to Corne et al (see Br.J.Pharmacol. 20, pp 106–120) is used to determine the ability of the compounds to induce a head-shaking syndrome in mice in interaction with a subthreshold dose of 5-HTP.

Male NMRI-mice having a body weight of 20–30 g are used. 60 min. prior to administration of the test compounds the animals are given an i.p. injection of 25 mg/kg of the MAO-inhibitor pargyline dissolved in a volume of 10 ml/kg of 2% tylose solution. Groups of 20 animals are used for each dose of the test compounds. The test compounds are administered per os in a volume of 10 ml/kg of 2% tylose solution. After 30 min. 50 mg/kg 5-HTP in a volume of 10 ml/kg of 2% tylose solution are injected i.p. and each animal is placed in a case individually. A group of control animals receives only the pargyline injection, the 5-HTP injection and 2% tylose solution p.o.

60 min. after administration of the test compounds (=30 min. after 5-HTP injection) the animals are observed for 120 sec. in order to check, whether or not the head-shaking-syndrome occurs.

The ED$_{50}$ is defined as the dose at which the number of animals showing a head-shake-syndrome is increased by 50% as compared with the control group. The results are given in the following table.

| Compound No. | Antidepressive Activity, inducement of head-shaking-syndrome by interaction with 5-HTP ED$_{50}$ μmol/kg p.o. |
|---|---|
| 3135 | 72 |
| 3142 | 74 |
| 3143 | 130 |

4. Evaluation of anxiolytic properties.

For evaluating the anxiolytic properties of the compounds a modified method according to Davidson et al (see The Benzodiazepines, Raven Press New York 1973 pp 327-345) is used, whereby the ability of the compounds to change the behavior of rats in a punishment conflict situation is examined.

In order to create the conflict situation the following experimental set up and procedure are used:

The tests are performed in Skinner boxes which are provided with an electrifyable grid-floor, a lever which has to be pressed by the rat, an automatic feeder and 2 different light sources. Female Wistar rats having a body weight of 180-300 g are used. Prior to testing the animals are trained to obtain food by pressing the lever, whereby 2 phases of different conditions alternate. The two phases are distinguished by different lightening. During one phase a food reward is given at a fixed ratio after each 10th lever press (=FR 10), yet simultaneous by with the food pellet an electric food shock punishment is delivered. During the other phase food reward is obtained without any electric punishment, yet lever pressing is rewarded with a food pellet far less frequently and at varying time intervals only (average interval 30 sec=VI30). During each 47 min. trial session 7 VI30 phases (300 sec. each) alternate with 6 FP10 phases (120 sec. each).

For testing the compounds each animal is subjected to the 47 min. test procedure once a day on 4 consecutive days always at the same time. On days 1, 2 and 3 the animals are given per os 10 ml/kg of 2% tylose soluton 60 min. prior to test begin. On day 4 they are given a dose of the test compound in the tylose solution. For each animal the number of lever press responses in the punished FR10 phases and in the unpunished VI30 phases are recorded seperately for each day. For each animal the mean values from the results of the first three days are taken as control values. The results from the 4th day are compared with these control values. The lowest doses which produce significant changes in the number of lever presses are determined for the unpunished phase and for the punished phase as the minimum effective doses (=MED$_{up}$ and ME$_{pp}$). Increased activity during the punished phase is due to anxiolytic effects of the test compound. Reduced activity during the unpunished phase is an indication of sedative effects of the compound. From the test results which are given in the following table it is seen, that the compound exhibit a favorably low ratio of MED$_{pp}$/MED$_{up}$, which is considerably lower than that of the well known diazepam.

| Compound No. | Behavioral changes in conflict situation | |
| --- | --- | --- |
| | MED$_{PP}$ μmol/kg p.o. | MED$_{UP}$ μmol/kg p.o. |
| 3107 | 14,7 | 147 |
| 3110 | 6,8 | >215 |
| 3304 | 21,5 | >215 |
| Diazepam (comparison) | 31,6 | 46,4 |

Based on the psychopharmacological activities described above the compounds of formula Ic and their pharmacologically acceptable acid addition salts are useful as medicaments in the treatment and prophylaxis of illnesses and functional disturbances of the central nervous system.

We claim:

1. A tetraoxo compound corresponding to the Formula Ic

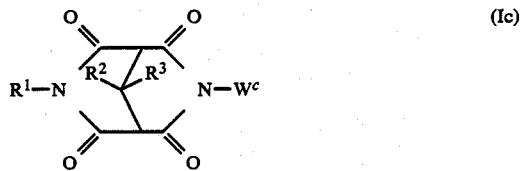

wherein
R$^1$ is a C$_1$-C$_{12}$ alkyl group, a C$_1$-C$_5$ alkenyl group in which the double bond is not adjacent the N-atom, or a C$_1$-C$_6$ alkyl group substituted by phenyl or C$_3$-C$_6$ cycloalkyl,
R$^2$ and R$^3$ are each independently a C$_1$-C$_7$ alkyl group or a phenyl group or together denote a C$_3$-C$_6$ alkylene group,
W$^c$ is a (CH$_2$)$_n$—Q$^c$ group, in which n is 2 to 10 and Q$^c$ is a group Z—R$^6$, where Z is a 1-piperazinyl group, and R$^6$ is in position 4 and is a phenyl group which is unsubstituted or is substituted by one or two substituents selected from the group consisting of lower alkyl, lower alkoxy, hydroxy, halogen, nitro, cyano, trifluoromethyl and C$_1$-C$_2$ alkylene dioxy, or is a pyridyl group which is unsubstituted or is substituted by a substituent selected from the group consisting of lower alkyl, nitro, halogen and lower alkoxy, or is a pyrimidyl group or a pyrazinal group; and acid addition salts of said compound.

2. A compound as claimed in claim 1, wherein R$^1$ contains 1 to 7 carbon atoms.

3. A compound as claimed in claim 2 wherein R$^1$ is an alkyl group containing 1 to 7 carbon atoms.

4. A compound as claimed in claim 2, wherein R$^1$ is an n-butyl group.

5. A compound as claimed in claim 1, wherein R$^1$ is a phenyl or cycloalkyl group linked via an alkylene group containing 1 to 3 carbon atoms with the associated N-atom of Formula (Ic).

6. A compound as claimed in claim 5, wherein said alkylene group is methylene.

7. A compound as claimed in claim 1, wherein at least one of R$^2$ and R$^3$ is an alkyl group containing 1 to 7 carbon atoms.

8. A compound as claimed in claim 7, wherein at least one of R$^2$ and R$^3$ is an alkyl group containing 1 to 4 carbon atoms.

9. A compound as claimed in claim 7, wherein R$^2$ and R$^3$ are the same.

10. A compound as claimed in claim 1, wherein the alkylene chain —(CH$_2$)$_n$— in Wc contains 2 to ≠carbon atoms.

11. A compound as claimed in claim 1, wherein R$^6$ is a phenyl group substituted by lower alkoxy or halogen.

12. A compound as claimed in claim 6, wherein R$^6$ is a monosubstituted phenyl group selected from the group consisting of 2-methoxy phenyl, 2-ethoxy phenyl and 4-chlorophenyl.

13. A compound as claimed in claim 6, wherein R$^1$ is an n-butyl group and R$^2$ and R$^3$ are each methyl groups.

14. The tetraoxo compound defined in claim 1, which is N-n-butyl-N'-(4-(4-(2-methoxyphenyl)-piperazin-1-yl)-butyl)-9,9-dimethyl-2,4,6,8-tetraoxo-3,7-diazabicyclo(3,3,1)-nonane and its acid addition salts.

15. The tetraoxo compound defined in claim 1, which is N-n-butyl-N'-(4-(4-(2-ethoxyphenyl)-piperazin-1-yl)- butyl)-9,9-dimethyl-2,4,6,8-tetraoxo-3,7-diazabicy-clo(3,3,1)-nonane and its acid addition salts.

16. A tetraoxo compound corresponding to Formula Ia or Ib

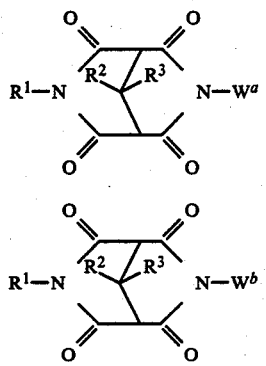

wherein
R¹ is a $C_1$-$C_{12}$ alkyl group, a $C_1$-$C_5$ alkenyl group in which the double bond is not adjacent the N-atom, or a $C_1$-$C_6$ alkyl group substituted by phenyl or $C_3$-$C_6$-cycloalkyl;
R² and R³ are each independently a $C_1$-$C_7$ alkyl or phenyl group or together denote a $C_3$-$C_6$ alkylene group,
$W^a$ is a $(CH_2)_n$—X group, in which n is 2 to 10 and W is a displaceable leaving group selected from the group consisting of halogen, tosylates, mesylate, sulfate and phosphate, and
$W^b$ is a $(CH_2)_n$—Z—H group wherein Z is a 1-piperazinyl group.

17. A compound as claimed in claim 15, wherein X is halogen selected from the group consisting of chlorine and bromine.

18. A method for preparing a compound corresponding to the Formula (Ic)

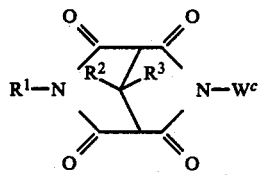

wherein
R¹ is a $C_1$-$C_{12}$ alkyl group, a $C_1$-$C_5$ alkenyl group in which the double bond is not adjacent the N-atom, or a $C_1$-$C_6$ alkyl group substituted by phenyl or $C_3$-$C_6$ cycloalkyl,
R² and R³ are each independently a $C_1$-$C_7$ alkyl group or a phenyl group or together denote a $C_3$-$C_6$ alkylene group,
$W^c$ is a $(CH_2)_n$—$Q^c$ group, in which n is 2 to 10 and $Q^c$ is a group Z—R⁶, where Z is a 1-piperazinyl group, and R⁶ is in position 4 and is a phenyl group which is unsubstituted or is substituted by one or two substituents selected from the group consisting of lower alkyl, lower alkoxy, hydroxy, halogen, nitro, cyano, trifluoromethyl and $C_1$-$C_2$ alkylene dioxy, or is a pyridyl group which is unsubstituted or is substituted by a substituent selected from the group consisting of lower alkyl, nitro, halogen and lower alkoxy, or is a pyrimidyl group or a pyrazinal group;
wherein a compound of Formula (I')

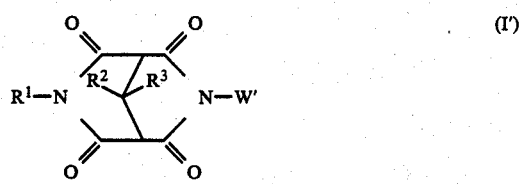

in which R¹, R² and R³ have the meanings defined above and W' is a hydrogen atom, a —$(CH_2)_n$—X group where X is a displaceable leaving group selected from the group consisting of halogen, tosylates, mesylate, sulfate and phosphate, or a —$(CH_2)_n$—Z—H group where Z is a 1-piperazinyl group and n is 2 to 10, is reacted with a compound of Formula (II)

$$Y-R^5 \quad (II)$$

where Y and R⁵ have the following meanings:
(a) if W' is a hydrogen atom, then
(a1) Y is a displaceable leaving group X and R⁵ is a —$(CH_2)_n$—$Q^c$ group where $Q^c$ is as defined above; or
(a2) if n=4 then Y is a

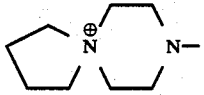

group, and R⁵ is the same as R⁶;
(b) if W' is a —$(CH_2)_n$—X group, then Y is a hydrogen atom and R⁵ is a —Z—R⁶ group where Z and R⁶ have the meanings defined above; or
(c) if W' is a —$(CH_2)_n$—Z—H group, then Y is a nucleophilically displaceable leaving group and R⁵ is an activated phenyl group which is substituted with an electron-withdrawing substituent selected from the group consisting of lower alkyl, lower alkoxy, hydroxy, halogen, nitro, cyano, trifluoromethyl and $C_1$-$C_2$ alkylene dioxy, or is a pyridyl grup which is unsubstituted or is substituted by a substituent selected from the group consisting of lower alkyl, nitro, halogen and lower alkoxy, or is a pyrimidal group or a pyrazinyl group.

19. A pharmaceutical composition comprising an effective central nervous system affecting amount of at least one compound corresponding to Formula (Ic):

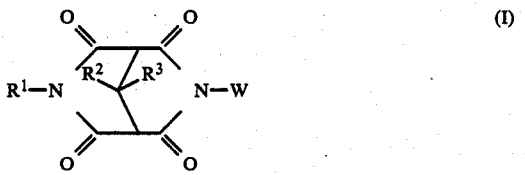

wherein R¹, R², R³ and $N^c$ are as defined in claim 1, or a pharmaceutically acceptable acid addition salt of said compound, and at least one conventional pharmaceutical carrier or adjuvant.

* * * * *